(12) United States Patent
Eagle

(10) Patent No.: US 8,905,020 B2
(45) Date of Patent: Dec. 9, 2014

(54) SPACER AND COMPONENTS THEREFOR

(76) Inventor: Allan Eagle, Springvale (AU)

(*) Notice: Subject to any disclaimer, the term of this patent is extended or adjusted under 35 U.S.C. 154(b) by 0 days.

(21) Appl. No.: 13/884,429

(22) PCT Filed: Feb. 24, 2011

(86) PCT No.: PCT/AU2011/000200
§ 371 (c)(1),
(2), (4) Date: Jul. 19, 2013

(87) PCT Pub. No.: WO2012/061866
PCT Pub. Date: May 18, 2012

(65) Prior Publication Data
US 2013/0291862 A1   Nov. 7, 2013

(30) Foreign Application Priority Data

Nov. 10, 2010   (AU) .................................. 14848/2010

(51) Int. Cl.
*A61M 15/00* (2006.01)
*A61M 16/00* (2006.01)
*A61M 39/24* (2006.01)
*A61M 39/10* (2006.01)

(52) U.S. Cl.
CPC ........... *A61M 15/0065* (2013.01); *A61M 39/24* (2013.01); *A61M 15/0086* (2013.01); *A61M 15/0016* (2013.01); *A61M 2039/1077* (2013.01); *A61M 15/009* (2013.01)
USPC ................................ 128/203.12; 128/200.14

(58) Field of Classification Search
USPC ............. 128/203.11–203.16, 200.21, 205.24, 128/200.14, 207.12, 207.16
See application file for complete search history.

(56) References Cited

U.S. PATENT DOCUMENTS

| 2,674,318 | A | * | 4/1954 | Sutliff ........................... 166/165 |
| 4,259,951 | A | | 4/1981 | Chernack et al. |
| 5,385,140 | A | | 1/1995 | Smith |
| 6,557,549 | B2 | * | 5/2003 | Schmidt et al. .......... 128/200.24 |
| 7,107,987 | B2 | * | 9/2006 | Sundaram et al. ....... 128/200.23 |
| 7,185,651 | B2 | * | 3/2007 | Alston et al. ............. 128/205.24 |
| 7,748,385 | B2 | * | 7/2010 | Lieberman et al. ...... 128/207.12 |

FOREIGN PATENT DOCUMENTS

| GB | 2 412 325 B | 2/2006 |
| JP | 2002-306597 A | 10/2002 |

OTHER PUBLICATIONS

International Search Report: mailed Apr. 27, 2011; PCT/AU2011/000200.
International Preliminary Report on Patentability dated May 14, 2013; PCT/AU2011/000200.
Writen Opinion of the International Search Authority; dated Apr. 27, 2011; PCT/AU2011/000200.

* cited by examiner

*Primary Examiner* — Justine Yu
*Assistant Examiner* — Kathrynn Reilly
(74) *Attorney, Agent, or Firm* — Flener IP Law; Zareefa Flener

(57) ABSTRACT

A spacer for delivering a medicinal substance is provided having a chamber having a tubular body defining a first reservoir, the top end of the body narrowing to define a single unobstructed central chamber aperture, a base for the body having an inlet for admission of the substance into the first reservoir, a vented member connected atop the body, a mouthpiece connected atop the vented member and partly defining a second reservoir, the mouthpiece having an outlet for withdrawal of the substance from the second reservoir The spacer also has a valve within the chamber having a self-supporting central domed portion and defining a central cross slit at its peak, the domed portion opening during inspiration and closing during expiration, and a flat ringed portion surrounding the domed portion with a circumferential free edge, the diameter of the ringed portion being approximately twice the diameter of the domed portion.

13 Claims, 8 Drawing Sheets

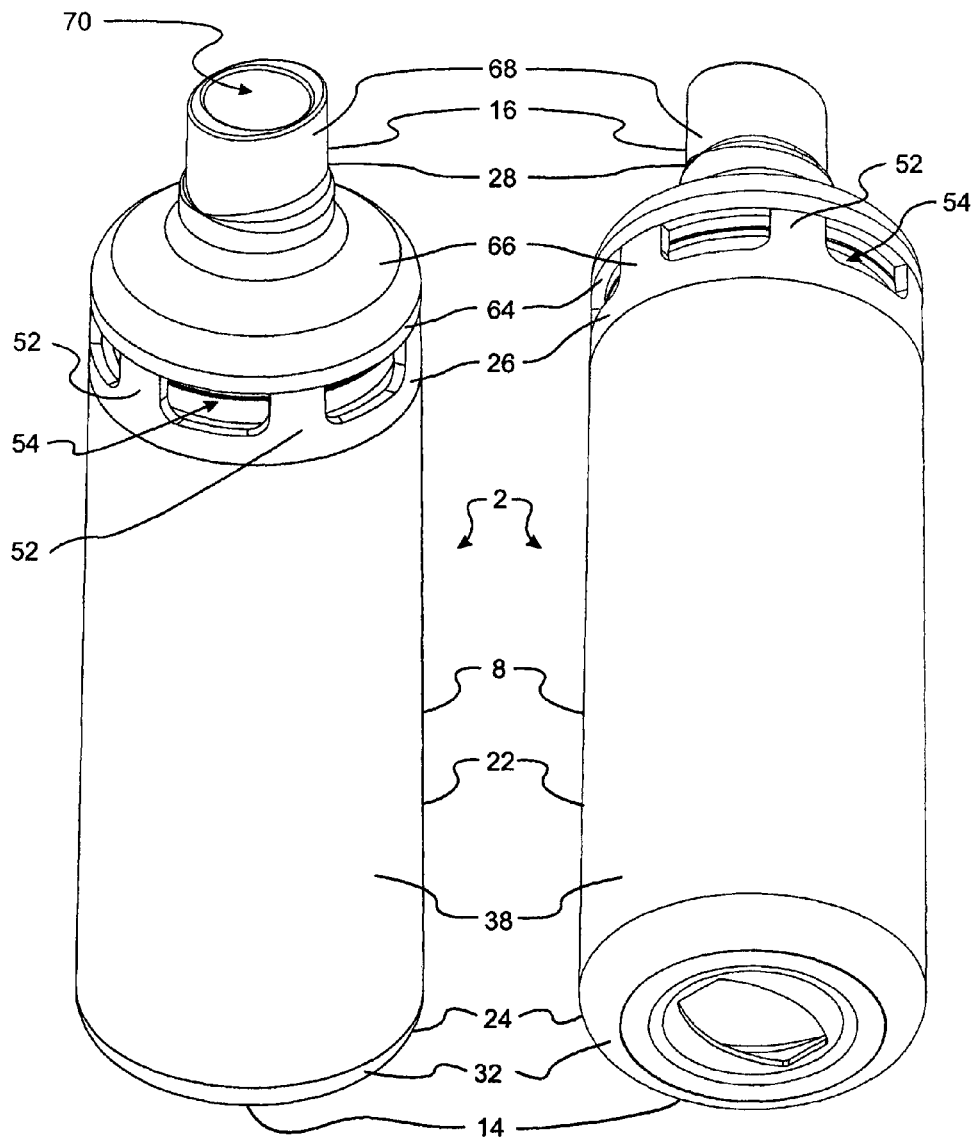
FIG. 1                    FIG. 2

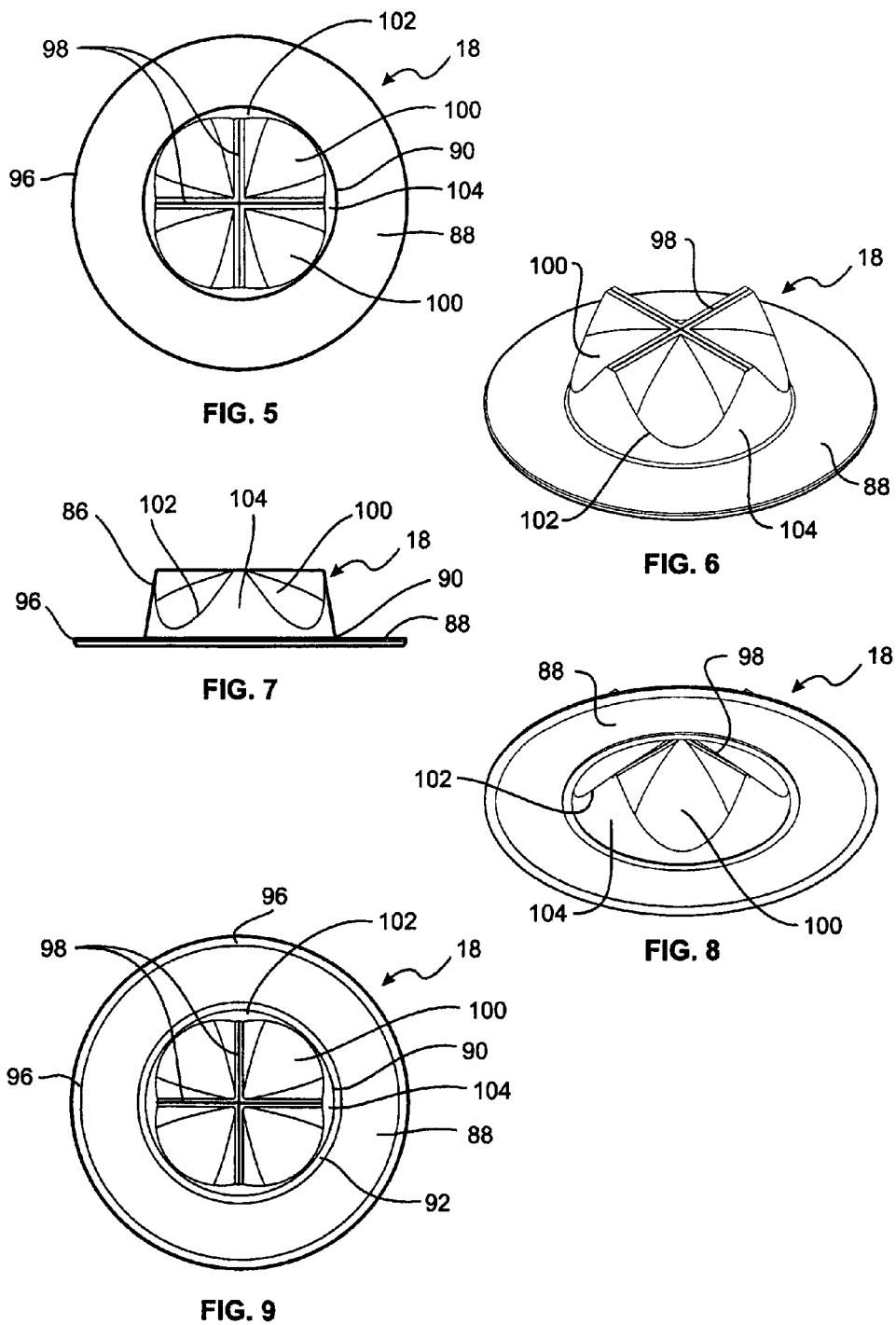

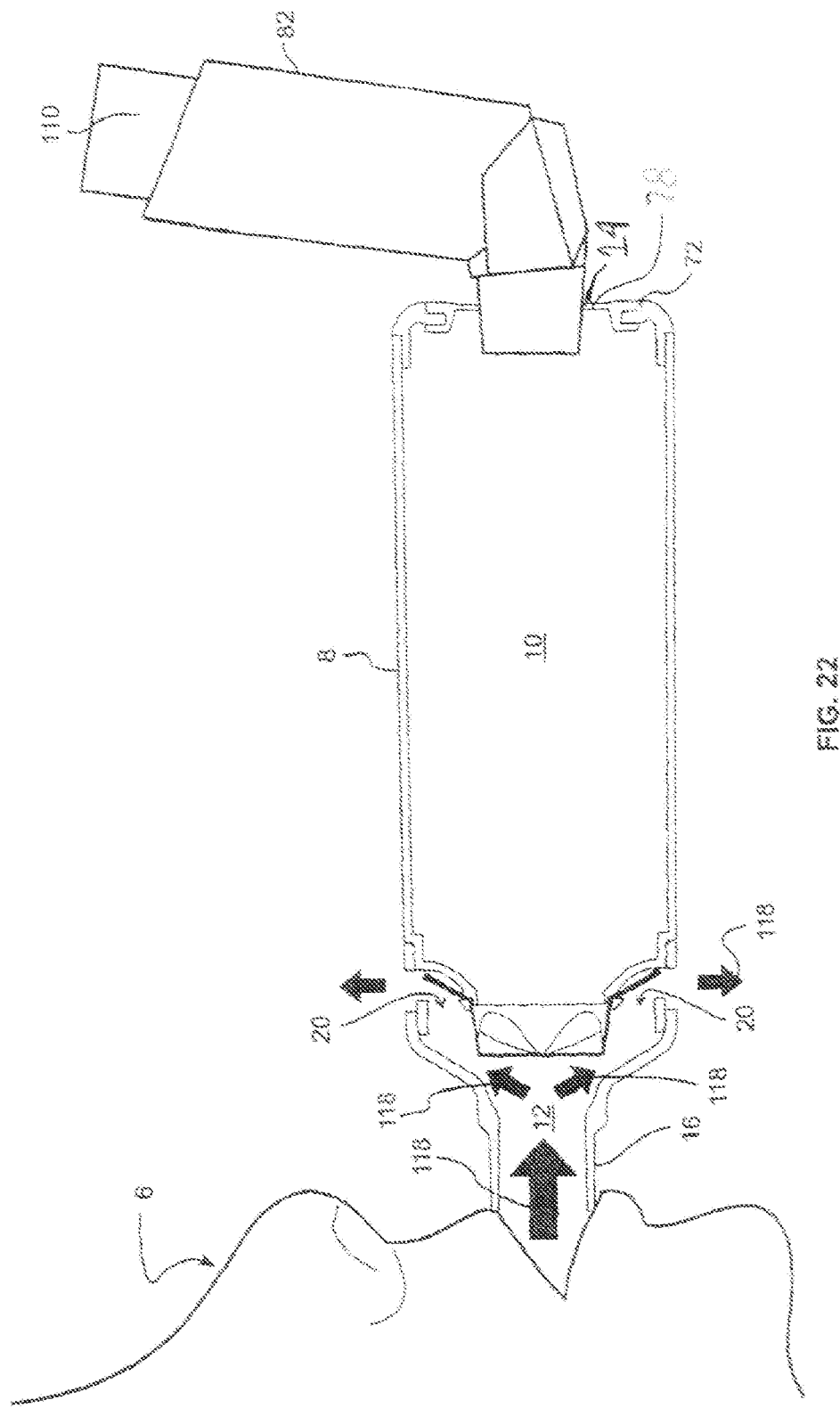

SPACER AND COMPONENTS THEREFOR

TECHNICAL FIELD

The present invention relates to a spacer and/or components therefor. In one particular aspect the invention relates to a flow valve for use in a spacer.

BACKGROUND ART

Any discussion of documents, devices, acts or knowledge in this specification is included to explain the context of the invention. It should not to be taken as an admission that any of the material forms a part of the prior art base or the common general knowledge in the relevant art in Australia or elsewhere on or before the priority date of the disclosure herein.

Sufferers of asthma or chronic obstructive pulmonary disease (COPD) often use a metered dose inhaler in order to inhale a bronchodilatory drug such as Salbutimol into their lungs, thereby opening up their pathologically constricted airways. However, if the patient is unable to co-ordinate spraying of the medication into their mouth (which is actuated by depressing a medication canister inside a housing of the inhaler), with a deep inspiratory breath, much of the medication may be deposited on the back of their mouth instead of being drawn deep into their lungs. A spacer may be particularly beneficial for patients struggling with this timing issue as the spacer allows the patient draw medication deep into the lungs by a process of spraying the medication into the spacer and then slowly and deeply breathing in and out, usually for about 5 to 10 breaths.

Whilst not being an admission of common general knowledge, U.S. Pat. No. 5,816,240 describes a spacer having: a chamber with a mouthpiece; an inspiratory valve with a radially extending disc and an axially extending plug retainer, the inspiratory valve being configured for opening on inspiration by a patient and closing upon expiration by a patient; and an expiratory valve comprising a radially extending ring, the inspiratory valve being configured for opening upon expiration by a patient and dosing upon inspiration by a patient.

A disadvantage of prior art spacers such as the one mentioned above may be the use of two valves which both move during inspiration and expiration, potentially causing increased resistance to flow and leading to overly complex designs. Another disadvantage with these types of spacers may be the need for ultrasonic welding of the chamber components, potentially adding to the complexity and reducing efficiency of assembly during manufacture.

Thus, it may be advantageous to provide a new spacer, or new component for a spacer, which reduces, limits, overcomes, or ameliorates some of the problems, drawbacks, or disadvantages associated with prior art devices, or provides an effective alternative to such devices.

DISCLOSURE OF THE INVENTION

In one aspect the invention provides a spacer for delivering a medicinal substance to a user, the spacer comprising:
a chamber comprising,
  first and second reservoirs,
  an inlet for admission of the medicinal substance into the first reservoir,
  an outlet for withdrawal of the medicinal substance from the second reservoir,
  a vent for expulsion of air from the second reservoir, and
a valve located at least partly within the chamber, the valve being adapted to,
  allow forward-flow of the medicinal substance from the first reservoir to the second reservoir during user inspiration,
  substantially limit inflow of air through the vent into the second reservoir during user inspiration,
  substantially limit backflow of the medicinal substance from the second reservoir to the first reservoir during user expiration, and
  allow expulsion of air from the second reservoir through the vent during user expiration.

The valve may be a unitary flow valve.

The valve may comprise a retaining portion which remains engaged with or retained by a part of the chamber. Further, the valve may comprise a first flow control portion which is anchored by the retaining portion.

The first flow control portion may be adapted to open during user inspiration, thereby enabling forward flow of the medicinal substance, and adapted to close during user expiration, thereby substantially limiting backflow of the medicinal substance.

The first flow control portion may comprise at least one substance flap member. The substance flap member may have a free edge which is adapted to flap open during opening of the second flow control portion and adapted to flap closed during closing of the first flow control portion.

In a suitable form the first flow control portion may comprise multiple flap members.

The first flow control portion may comprise two substance flap members having free edges which are adapted to close together when the first flow control portion is closed and adapted open apart when the first flow control portion is open. In a suitable form, the substance flap members may resemble a duck bill.

The first flow control portion may comprise four substance flap members having free edges which are adapted to close together when the first flow control portion is closed and adapted open apart when the first flow control portion is open. The free edges may form a cross slit. The substance flap members may form quadrant portions.

The first flow control portion may form a domical-like shape.

The first flow control portion may be angled upwardly and inwardly by between 1 and 20 degrees. In a suitable form it may be angled upwardly and inwardly by between 5 and 15°. Preferably it may be angled upwardly and inwardly by about 10°.

The first flow control portion may be between 5 and 15 mm in height. Preferably it may be about 10 mm in height.

The valve may comprise a second flow control portion which is anchored by the retaining portion.

The second flow control portion may be adapted to close during user inspiration, thereby substantially limiting outside air from flowing through the vent into the second reservoir.

The second flow control portion may be adapted to open during expiration, thereby enabling expulsion of air through the vent from the second reservoir.

The second flow control portion may comprise an air flap member. The air flap member may have a free edge which is adapted to flap open during user expiration and adapted to flap closed during user inspiration.

The air flap member may have a circumferential free edge. It may be disc shaped.

The first control portion may be centrally placed in the valve. Suitably, the second flow control portion may surround the first control portion. The retaining portion may be located between the first control portion and the second control portion.

The chamber may comprise a first chamber portion. Suitably the first chamber portion may, along with the valve, substantially define the first reservoir. The first chamber portion may comprise a tubular member The chamber may comprise a second chamber portion. In a suitable form, the second chamber portion may, along with the valve, substantially define the second reservoir. The second chamber portion may comprise a vented member. The vented member may define the vent. Suitably, the second chamber portion may comprise a mouthpiece which is attached to or continuous with the vented member.

The retaining portion of the valve may be fixedly sandwiched between the tubular member and the vented member.

The vented member may comprise a central chamber aperture. Further, the vented member may comprise a series of radially disposed apertures which surround the chamber aperture. The radially disposed apertures may form part or all of the vent.

The inlet may comprise a flexible portion with an aperture which can adapt to and snugly receive medicinal substance delivery devices of various shapes and sizes.

Suitably, the inlet may form part of a base of the chamber which is detachable from the remainder thereof.

User inspiration and/or user expiration may be passive, or mechanically assisted or controlled. For example, a user's breathing may be assisted or forced by a machine such as a ventilator.

The outlet may comprise the mouthpiece. Suitably, the outlet may be adapted for insertion into the user's mouth. Additionally or alternatively, the outlet may be adapted for connection with a device which may be disposed in or about the user's mouth. For instance, the outlet may be connected with an oxygen mask placed over the user's mouth and nose, or a ventilator tube extending into the user's mouth.

The medicinal substance may comprise a drug. Suitably, the medicinal substance may comprise a powder in suspension, an atomised liquid, or a fluid.

In another aspect the invention may provide a unitary valve for use with a spacer chamber for delivering a medicinal substance to a user, the spacer chamber comprising, first and second reservoirs, an inlet for admission of the medicinal substance into the first reservoir, an outlet for withdrawal of the medicinal substance from the second reservoir, and a vent for expulsion of air from the second reservoir, the valve comprising:
- a retaining portion which is adapted to be retained by a part of the chamber,
- a first flow control portion which is adapted to be anchored by the retaining portion, the first flow control portion being adapted to open during user inspiration, thereby allowing forward-flow of the medicinal substance from the first reservoir to the second reservoir, and adapted to close during user expiration, thereby substantially limiting backflow of the medicinal substance from the second reservoir to the first reservoir, and
- a second flow control portion which is adapted to be anchored by the retaining portion, the second flow control portion being adapted to close during user inspiration, thereby substantially limiting inflow of air through the vent into the second reservoir, and adapted to open during expiration, thereby allowing expulsion of air from the second reservoir through the vent.

BRIEF DESCRIPTION OF THE DRAWINGS

In order that the invention may be more clearly understood and put into practical effect there shall now be described in detail preferred constructions of apparatus and methods for spacers and components therefor in accordance with the invention. The ensuing description is given by way of non-limitative examples only and is with reference to the accompanying drawings, wherein:

FIG. 1 is an above axonometric view of a spacer in accordance with a preferred embodiment of the invention;

FIG. 2 is a beneath axonometric view of the spacer;

FIG. 5 is a top view of a valve of the spacer in its resting configuration;

FIG. 6 is an above axonometric view of the valve in its resting configuration;

FIG. 7 is a side view of the valve in its resting configuration;

FIG. 8 is a beneath axonometric view of the valve in its resting configuration;

FIG. 9 is a bottom view of the valve in its resting configuration;

MODES FOR CARRYING OUT THE INVENTION

Figure 21:
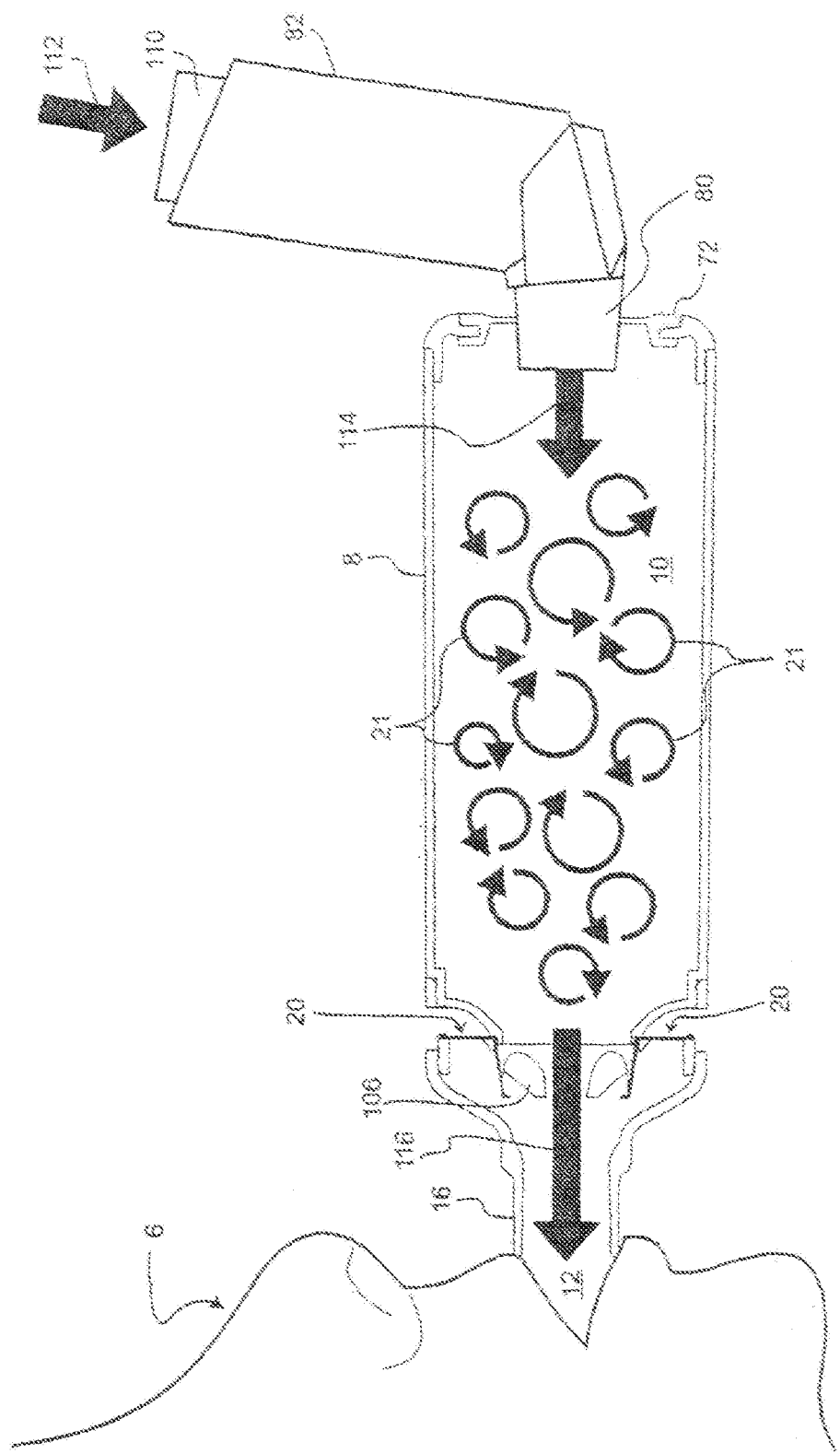
FIG. 21 is a diagrammatic view showing flow of medication from the inhaler into the spacer, and the flow pathway during user inspiration; and, FIG. 22 is a diagrammatic view of the spacer in use showing the flow pathway during user expiration.

Referring to the drawings, there is shown a spacer, generally designated 2, which is suitable for delivering aerosolised medication 4 to a user 6 (see FIG. 21 in particular).

The spacer 2 comprises a Makrolon polycarbonate chamber 8 and a flow valve 18 located within the chamber 8.

The chamber 8 comprises:
- a first reservoir 10 and a second reservoir 12 (see FIGS. 20-22);
- an inlet 14 for admission of aerosolised or powdered medication 4 into the first reservoir 10;
- an outlet 16 for withdrawal of the medication 4 from the second reservoir 12; and
- a vent 20 for expulsion of air from the second reservoir 12.

The flow valve 18 is adapted to:

allow forward-flow of the medication from the first reservoir 10 to the second reservoir 12 during user inspiration;

substantially limit inflow of air through the vent 20 into the second reservoir 12 during user inspiration;

substantially limit backflow of the medication or air from the second reservoir 12 to the first reservoir 10 during user expiration; and allow expulsion of air from the second reservoir 12 through the vent 20 during user expiration.

The chamber 8 comprises first and second chamber portions, the first chamber portion comprises a tubular member 22, and a detachable base member 24. The second chamber portion comprises a vented member 26 connected atop the tubular member 22, and a mouthpiece 28 connected atop vented member 26.

The base member 24 comprises a cylindrical ridge 30 which is stepped inwardly and upwardly from a curved cylindrical ring 32. A circular flange 34 projects inwardly from the cylindrical ring 32, the circular flange 34 having a series of spaced circular apertures 36.

The tubular member 22 comprises a cylindrical wall 38. Towards the bottom of the cylindrical wall 38 is a slight inwardly projecting ridge 40. The inwardly projecting ridge 40 articulates with the cylindrical ridge 30 during fitted insertion of the base member 24 into the tubular member 22. An attachment portion 42 is stepped in atop the cylindrical wall 38, the attachment portion 42 comprising a series of attachment ridges 44. A curved top portion 46 extends inwardly and upwardly from attachment portion 42, the curved top portion 46 ending to define a chamber aperture 48.

Vented member 26 comprises an attachment portion 48 having inwardly disposed attachment grooves 50 which are adapted for permanent engagement with the attachment ridges 44, thereby enabling permanent attachment of the vented member 26 with the tubular member 22 when assembling the product during manufacture. A series of spaced rectangular pillars 52 extend upwardly from the attachment portion 48, the pillars 52 defining the lower and side boundaries of a series of spaced circumferential apertures 54. The top boundary of the circumferential apertures is defined by a circular band 56 which is fixedly grasped by and within the top ends of the rectangular pillars 52. The top edge of the circular band 56 is angled in for attachment to mouthpiece 28. Extending inwardly from the circular band 56, and in alignment with the top ends of respective rectangular pillars 52, is a series of spaced transverse columns 58 which end in a retaining ring 60 for engaging flow valve 18. The transverse columns 58 form the side boundaries, while the retaining rings 60 and circular band 56 form the inner and outer boundaries respectively, of a series of spaced transverse apertures 62. The transverse apertures 62 form the openings of the vent 20, which vent 20 is continuous with the circumferential apertures 54.

The mouthpiece 16 comprises an attachment rim 64 for attachment with the circular band 56 of the vented member 26. A cupola portion 66 curves upwardly and inwardly from the attachment rim 64, before continuing into the tubular mouth portion 68, into which mouth aperture 70 opens.

The spacer 2 further comprises a flexible circular Santoprene rubber inlet moulding 72. The inlet moulding 72 comprises an externally facing C-shaped ring 74, with its upper and lower flanges grasping the circular flange 34 of the base member 24 therebetween. In the mouth of the "C" is a series of spaced mould pillars 76 which interconnect the upper and lower flanges of the mouth. The mould pillars 76 extend through respective apertures 36 of the base member 24, thereby firmly holding the inlet moulding 72 in place with respect to the base member 24. Extending inwardly from the base of the C-shaped ring 74 is a flexible inhaler flange 78. The inhaler flange 78 defines an inhaler aperture 84 which in this instance corresponds with the size and shape of an inhaler mouthpiece 80 (see FIG. 20) of a commonly available Salbutimol inhaler 82. It should be noted, however, that the flexible nature of inlet moulding 72, and in particular the inhaler flange 78, enables the inhaler aperture 84 to fitably adapt to other inhalers and medication administering devices of various shapes and sizes.

Silicone flow valve 18 comprises a domical-like first flow control portion 86. The first flow control portion 86 extends upwardly from a second flow control portion in the form of a circular flow ring 88 which is substantially flat when in its resting state inside the chamber 8. At and about the intersection between first flow control portion 86 and flow ring 88, is a functional retaining portion 90. The retaining portion is retained between the top free edge of the top portion 46 (which defines the chamber aperture 94 of the tubular member 22), and the under-surface of the retaining ring 60 (of the vented member 26).

Thus, the retaining portion 90 of flow valve 18 remains fixed, sandwiched between the tubular member 22 and the vented member 26. The retaining portion 90 includes a thickening in the flow valve 18 at the intersection between the first flow control portion 86 and the flow ring 88. The thickening itself comprises a small circular internal ridge 92 which may assist in limiting slipping of the flow valve 18 between the edge of the chamber aperture 94 and the retaining ring 60. The outer free edge of the flow ring 88 also comprises a thickened free edge 96.

The domical-like first flow control portion 86 comprises a cross slit 98 which is closed when the valve is in its resting state. The cross slit 98 marks the free edges of four quadrant portions 100. The remainder of each of the quadrant portions is defined by a U-shaped edge 102, the arms of which extend downwardly from the ends of the cross slit 98. A crown shaped portion 104 extends upwardly from retaining portion 90, with the triangular peaks of the crown extending between, and meeting with, the U-shaped edges 102 of the quadrant portions 100.

In a preferred version of the illustrated embodiment, the flow ring 88, U-shaped crown portion 104, and quadrant portions 100 of the flow valve 18 are of 3 mm thickness. The diameter of the flow ring 88 is 43.5 mm, while the diameter of the first flow control portion is 24.3 mm at its base and 22 mm at its top. Thus the first flow control portion 86 is angled in from its base to its top. In this instance the U-shaped crown portion 104 is angled upwardly and inwardly by about 10°, although it is envisaged that the angle may be between 1 and 20 degrees in alternative embodiments. In this instance, the height of the first flow control portion 86 when closed is 10 mm.

The resting configuration of the flow valve 18 when inside the chamber 8 is shown in FIGS. 5-9. In its resting configuration, the cross slit 98 of the first flow control portion 86 is closed, and the flow ring 88 is flatly disposed, level with retaining portion 90.

In FIGS. 10-14, the valve 18 is shown in its inspiration configuration when retained within the chamber 8. In this configuration, the free edges of quadrant portions 100 flap upwardly and outwardly, thereby creating a four point star shaped inhalation opening 106 through which air flows, (as indicated by arrow 108) during user inspiration.

FIGS. 15-19 show the expiration configuration of flow valve 18 when inside the chamber 8. In the expiration configuration, the cross slit 98 is again closed, but the flow ring 88, which is anchored at retaining portion 90, flaps downwardly at its free edge 96 as a result of pressure from expiratory flow (as indicated by arrows 110).

Figures 3, 4:
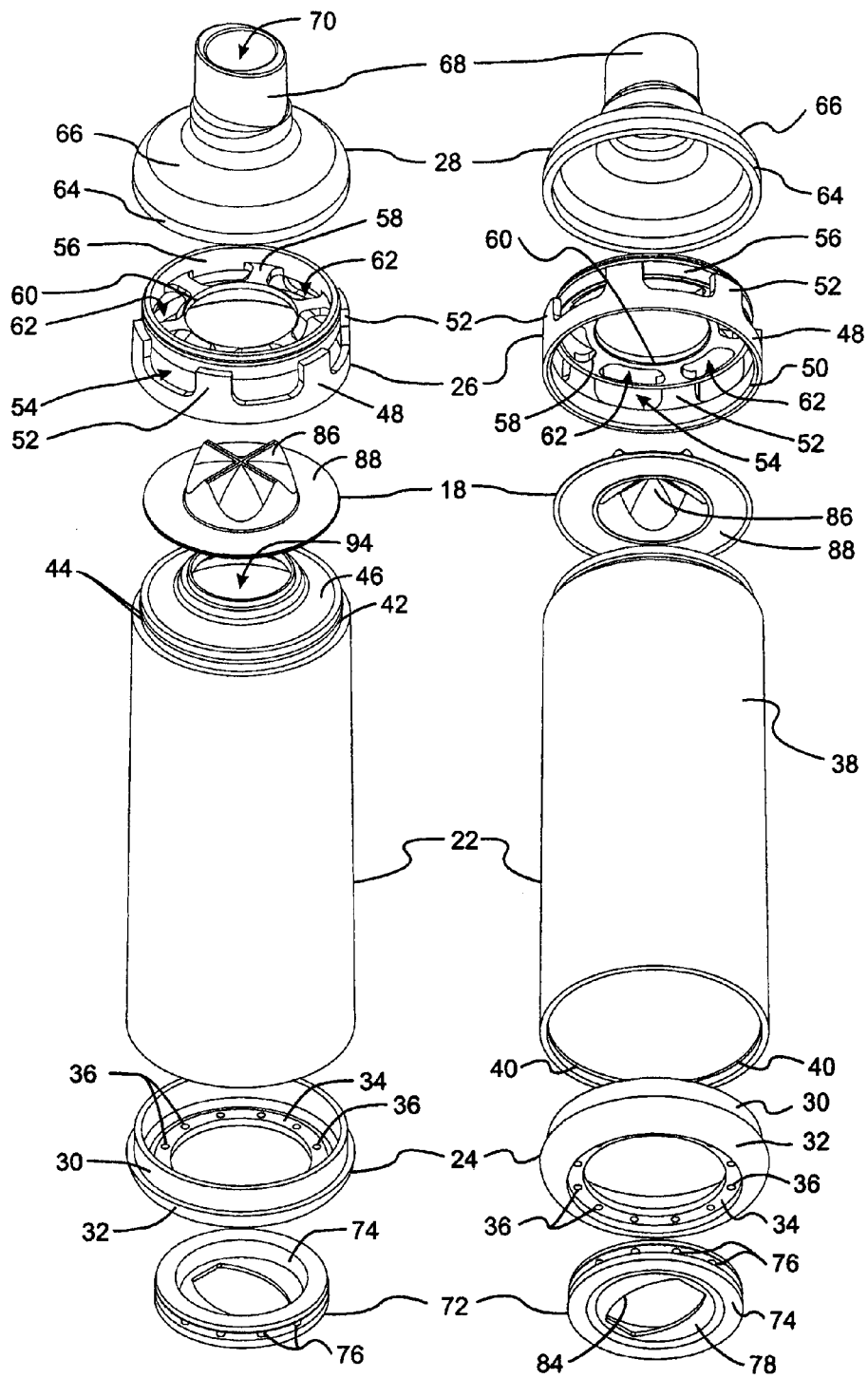
FIG. 3 is an exploded axonometric view of the spacer from above.
FIG. 4 is an exploded axonometric view of the spacer from below.
Figure 10:
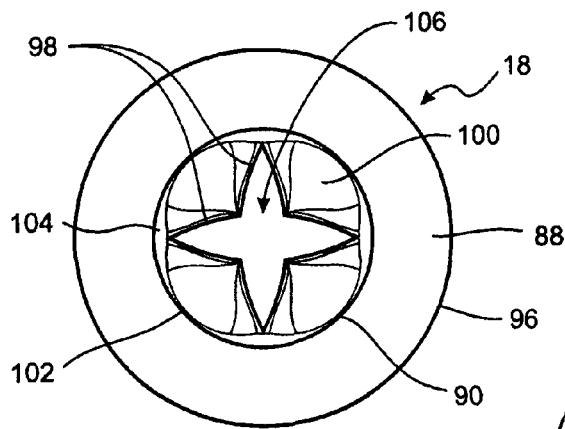
FIG. 10 is a top view of the valve in its inspiration configuration.
Figure 11:
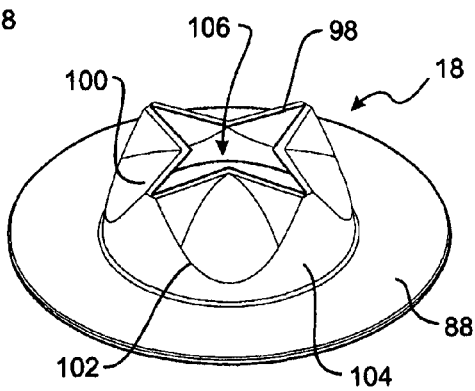
FIG. 11 is an above axonometric view of the valve in its inspiration configuration.
Figure 12:
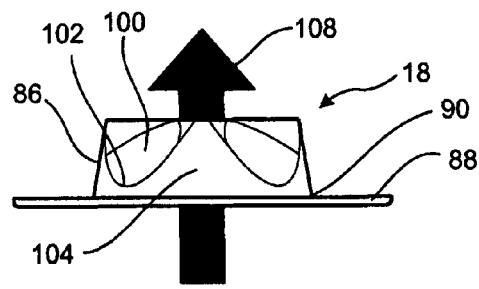
FIG. 12 is a side view of the valve in its inspiration configuration
Figure 13:
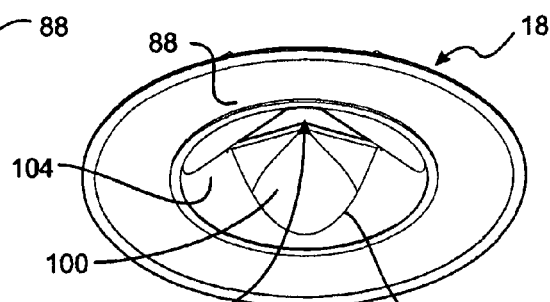
FIG. 13 is a bottom axonometric view of the valve in its inspiration configuration.
Figure 14:
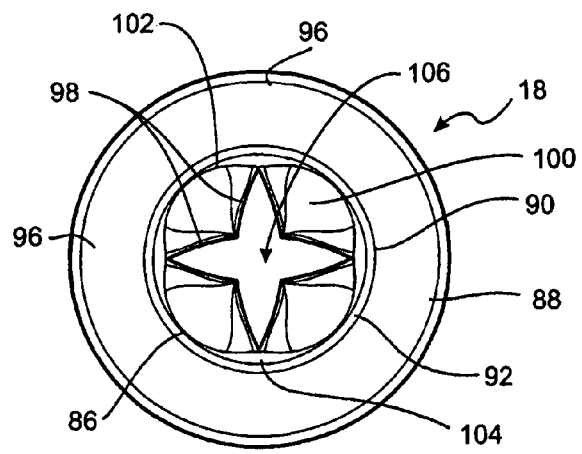
FIG. 14 is a bottom view of the valve in its inspiration configuration.
Figure 15:
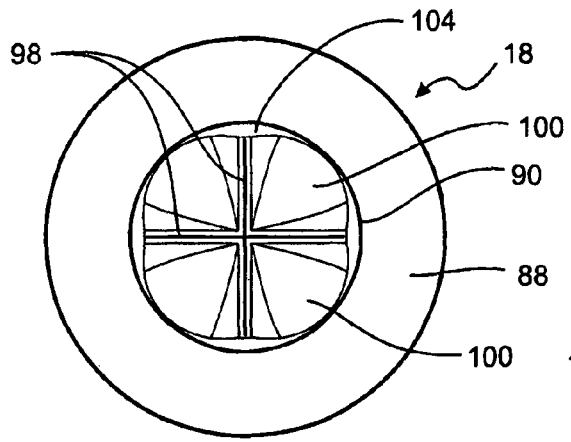
FIG. 15 is a top view of the valve in its expiration configuration.
Figure 16:
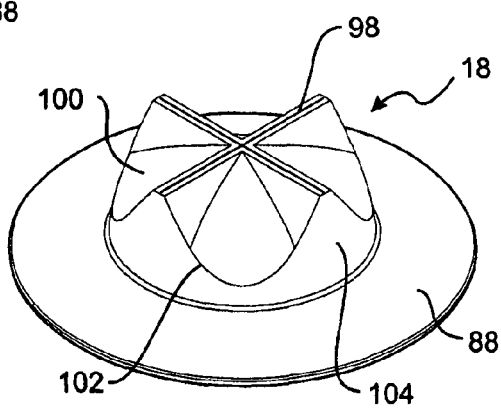
FIG. 16 is an above axonometric view of the valve in its expiration configuration.
Figure 17:
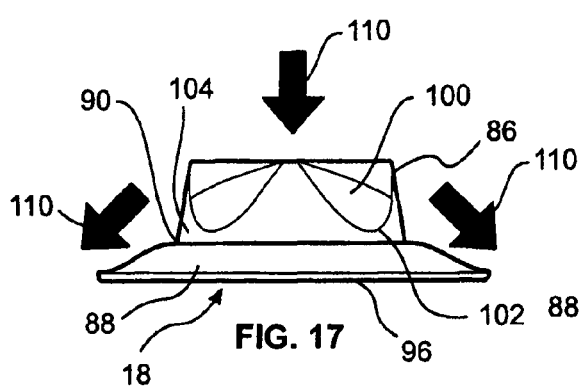
FIG. 17 is a side view of the valve in its expiration configuration.
Figure 18:
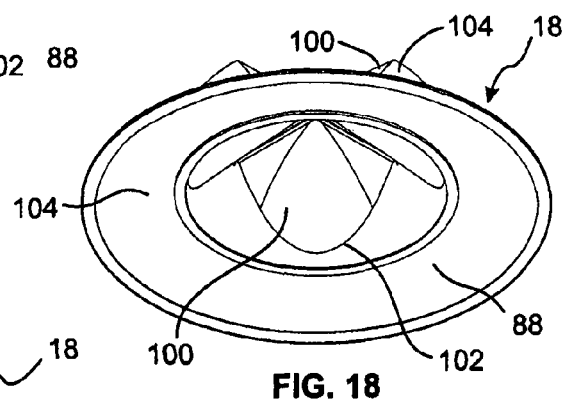
FIG. 18 is a bottom axonometric view of the valve in its expiration configuration.
Figure 19:
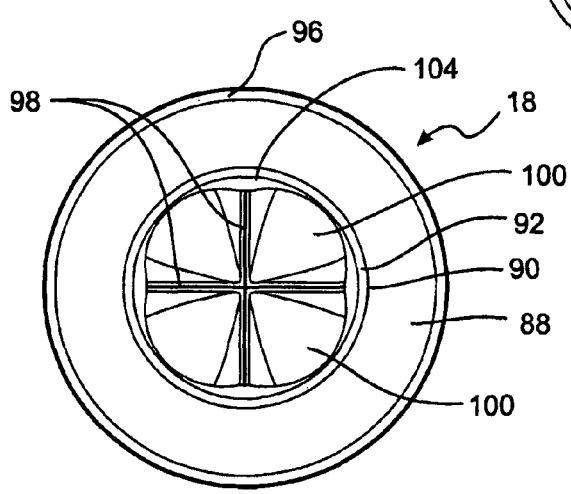
FIG. 19 is a bottom view of the valve in its expiration configuration.
Figure 20:
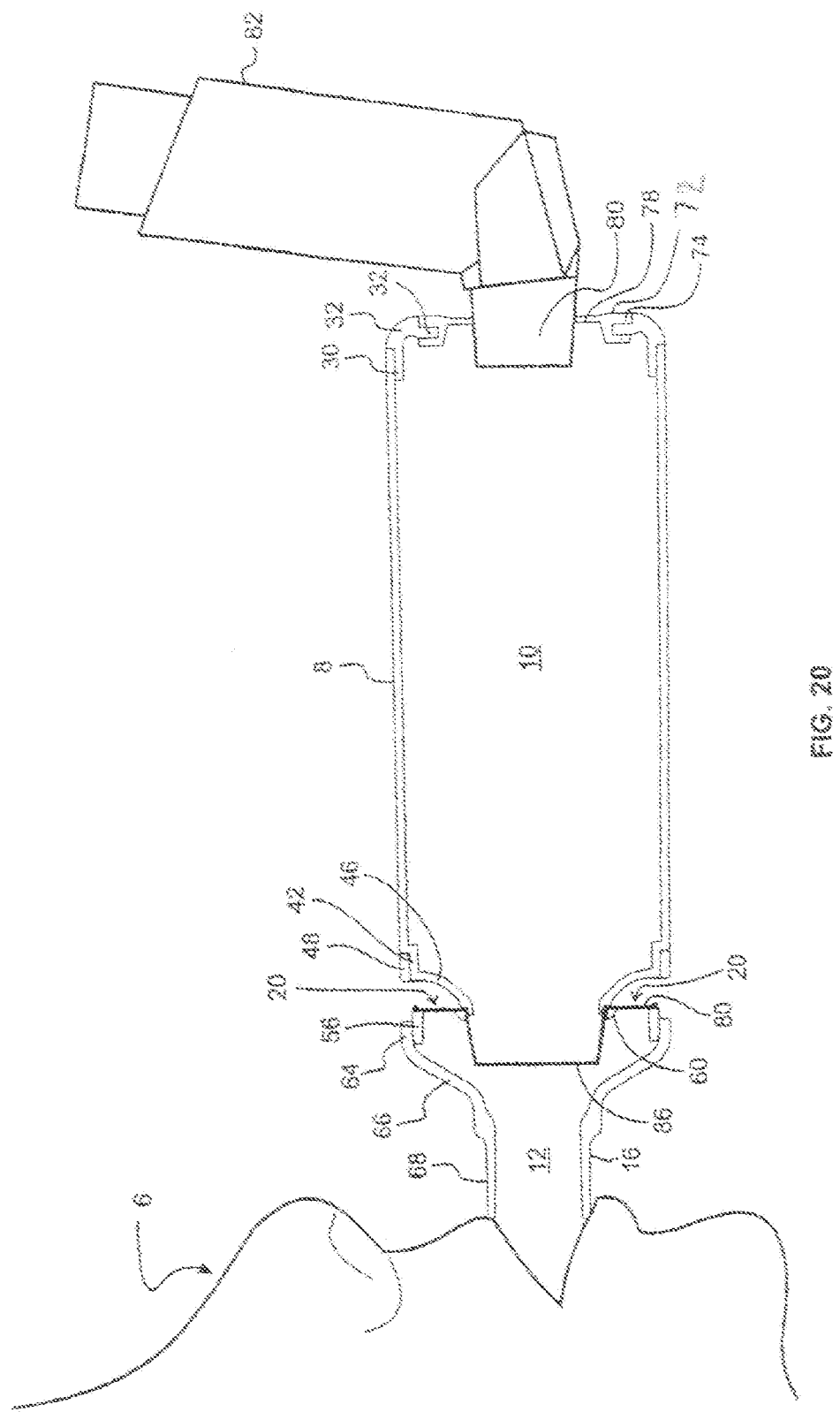
FIG. 20 is a diagrammatic view showing a spacer positioned for use, wherein an outlet of the spacer is placed in the mouth of a user and a medication inhaler is inserted into an inlet of the spacer.

The spacer 2 may be used in the following manner:

As illustrated in FIG. 20, the inhaler mouthpiece 80 of the Salbutimol inhaler 82 is inserted snugly into the inhaler aperture 84 of the flexible inlet moulding 72, and then the mouth portion 68 of mouthpiece 28 is inserted into the mouth of the user 6. The flow valve 18 can be seen in its resting configuration with both the first flow control portion 86 and the flow ring 88 being closed.

The Salbutimol inhaler's pressurised canister 110 is depressed by the user 6, (as indicated by arrow 112), thereby causing aerosolised fluid Salbutimol particles to be sprayed out through inhaler mouth piece 80 (as indicated by arrow 114) so that the Salbutimol particles (as indicated by arrow 21) collect within the first reservoir 10 of the chamber 8.

The user 6 then inspires causing reduced air pressure in the second reservoir 12 of the chamber 8. This in turn causes the first flow control portion 86 of flow valve 18 to flap open and air in the second reservoir 12, (which includes Salbutimol fluid particles 21) to be drawn through the inhalation opening 106, into the second reservoir 12, and through to the mouth of the user 6 (as indicated by arrow 116).

As illustrated in FIG. 22, the user 6 then exhales, (with expiratory flow being indicated by arrows 118 and expiratory air flows back towards flow valve 18, forcing the quadrant portions 100 of the first flow control portion 86 to flap back to their closed position, and forcing the flow ring 86 to flap open, thereby opening access to vent 20 which enables expiratory air to flow out of chamber 8.

The process repeats as the user inhales and exhales.

While this invention has been described in connection with specific embodiments thereof, it will be understood that it is capable of further modification(s). The present invention is intended to cover any variations, uses or adaptations of the invention following in general, the principles of the invention and including such departures from the present disclosure as come within known or customary practice within the art to which the invention pertains and as may be applied to the essential features hereinbefore set forth.

Finally, as the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the attached claims. Various modifications and equivalent arrangements are intended to be included within the spirit and scope of the invention. Therefore, the specific embodiments are to be understood to be illustrative of the many ways in which the principles of the present invention may be practiced.

Where the terms "comprise", "comprises", "comprised" or "comprising" are used in this specification, they are to be interpreted as specifying the presence of the stated features, integers, steps or components referred to, but not to preclude the presence or addition of one or more other features, integers, steps, components to be grouped therewith.

The claims defining the invention are as follows:

1. A spacer for delivering a medicinal substance to a user, the spacer comprising:
   a chamber comprising,
   tubular member at least partly defining a first reservoir, the top end of the tubular member narrowing to define a single unobstructed central chamber aperture,
   a base for the tubular member having an inlet for admission of the medicinal substance into the first reservoir,
   a vented member disposed on the tubular member, the vented member defining multiple transverse apertures positioned around the central chamber aperture and multiple circumferential apertures perpendicular to, at least partly beneath, and adjacent to, the transverse apertures, the transverse apertures forming the opening of a vent, which vent passes to and ends in the circumferential apertures,
   a mouthpiece disposed on the vented member, the mouthpiece partly defining a second reservoir, the mouthpiece having an outlet for withdrawal of the medicinal substance from the second reservoir, and
   a valve located at least partly within the chamber, the valve comprising,
   a retaining portion which is retained by a part of the chamber,
   a first flow control portion forming a dome structure at rest which is anchored by and extends upwardly from the retaining portion, the dome structure being self-supporting so as to inherently resist against collapse beyond its resting state on exhalation by a user, the dome structure defining a central cross slit proximate its peak, the first flow control portion being adapted to open during user inspiration, thereby allowing forward-flow of the medicinal substance from the first reservoir to the second reservoir, and adapted to close during user expiration, thereby substantially limiting backflow of the medicinal substance from the second reservoir to the first reservoir, and
   a flat ring shaped second flow control portion which surrounds the first flow control portion, is anchored by the retaining portion, and has a circumferential free edge, the diameter of the second flow control portion being approximately twice the diameter of the first flow control portion, the second flow control portion being adapted to close during user inspiration, thereby closing off the transverse apertures and substantially limiting inflow of air through the vent into the second reservoir, and adapted to open during expiration, its free edge flapping downwardly away from the transverse apertures and beneath the roof of the circumferential apertures, thereby allowing expulsion of air from the second reservoir through the vent.

2. The spacer according to claim 1 wherein, the first flow control portion comprises four flap members which are adapted flap open during user expiration and adapted to flap closed during user inspiration.

3. The spacer according to claim 2 wherein each of the four flap members comprise a respective quadrant portion, the quadrant portions having free edges which together form the cross slit.

4. The spacer according to claim 2 wherein the air flap member has a circumferential free edge.

5. The spacer according to claim 1 wherein the chamber comprises:
   a first chamber portion which, along with the valve, substantially defines the first reservoir, the first chamber portion comprising a tubular member, and a second chamber portion which, along with the valve, substantially defines the second reservoir, the second chamber portion comprising a vented member which defines the vent and a mouthpiece which is attached to or continuous with the vented member.

6. The spacer according to claim 5 wherein the valve is fixedly sandwiched between the tubular member and the vented member.

7. The spacer according to claim wherein the inlet comprises a flexible portion with an aperture capable of adapting to and snugly receiving medicinal substance delivery devices of various shapes and sizes.

8. The spacer according to claim 1 wherein the inlet forms part of a base of the chamber which is detachable from the remainder thereof.

9. The spacer according to claim 1 wherein the outlet is adapted for connection with a device which may be disposed in or about the mouth of the user.

10. The spacer according to claim 1 wherein the first flow control portion is angled upwardly and inwardly by between 1 and 20 degrees.

11. The spacer according to claim 3 wherein the air flap member has a circumferential free edge.

12. The spacer according to claim 6 wherein the vented member comprises:

a central chamber aperture, and a series of radially disposed apertures which surround the central aperture and form part or all of the vent.

13. The spacer according to claim 1 wherein, the dome-like structure comprises a peripheral wall which extends upwardly from the retaining member into four crown peaks, and the cross slit spans between the four crown peaks.

* * * * *